United States Patent
Heuscher et al.

(10) Patent No.: US 6,510,337 B1
(45) Date of Patent: Jan. 21, 2003

(54) MULTI-PHASE CARDIAC IMAGER

(75) Inventors: Dominic J. Heuscher, Aurora, OH (US); Shalabh Chandra, Mayfield Heights, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 107 days.

(21) Appl. No.: 09/713,752

(22) Filed: Nov. 15, 2000

Related U.S. Application Data

(60) Provisional application No. 60/167,571, filed on Nov. 26, 1999.

(51) Int. Cl.[7] .............................................. A61B 5/0452
(52) U.S. Cl. ................................. 600/428; 378/8; 378/95
(58) Field of Search ............................. 600/428, 508, 600/519, 521, 523; 378/4, 8, 95

(56) References Cited

U.S. PATENT DOCUMENTS

| | | | |
|---|---|---|---|
| 4,547,892 A | 10/1985 | Richey et al. ................ 378/8 |
| 4,649,930 A | 3/1987 | Groch et al. ................ 128/695 |
| 5,997,883 A | 12/1999 | Epstein et al. ............... 424/306 |
| 6,275,560 B1 * | 8/2001 | Blake et al. .................... 378/8 |
| 6,298,111 B1 * | 10/2001 | Ozaki ............................ 378/8 |

FOREIGN PATENT DOCUMENTS

DE          19811360          10/1998

* cited by examiner

Primary Examiner—Peter Nerbun
(74) Attorney, Agent, or Firm—Fay, Sharpe, Fagan, Minnich & McKee, LLP

(57) ABSTRACT

A method of cardiac gating for use in an imaging apparatus includes monitoring a patient's cardiac cycle, and determining a cardiac cycle time for the patient. A desired cardiac phase of interest is selected, and a delay from a reference point in the cardiac cycle is determined. The delay is a function of the selected cardiac phase and the cardiac cycle time. Finally, the selected cardiac phase is located in the cardiac cycle using the delay. This cardiac gating method compensates for non-uniform changes in the patient's cardiac cycle corresponding to a non-uniform distribution of cardiac phases in the patient's cardiac cycle.

19 Claims, 3 Drawing Sheets

MULTI-PHASE CARDIAC IMAGER

This application claims the benefit of U.S. Provisional Application No. 60/167,571, filed Nov. 26, 1999.

BACKGROUND OF THE INVENTION

The present invention relates to the art of medical diagnostic cardiac imaging. It finds particular application in conjunction with computed tomography (CT) scanners, and will be described with particular reference thereto. However, it is to be appreciated that the present invention is also amenable to other like applications including other imaging modalities, such as, e.g., magnetic resonance imaging (MRI), electron beam CT (EBCT), etc.

Cardiac imaging is an important application for medical diagnostic imaging. Presently, there are a number of different imaging modalities which address the task, such as, e.g., CT, MRI, and the like. The goal is to image the heart at any selected one or more of the multiple phases of the cardiac cycle. This allows visualization of the coronary arteries for coronary artery disease, wall motion abnormalities, valve abnormalities, and other pathology. It is, therefore, desirable to identify accurately the different phases of the heart which have physiologic significance, and, to be able to identify these phases as the heart rate for a given patient varies, and also for different patients varying in age, gender, and physical condition.

Accordingly, in a preferred embodiment, one purpose of the present invention is to provide for an algorithm/model, and an apparatus for implementing the same, that uses the heart rate to automatically calculate or otherwise determine the different phases of the heart as the heart rate of the patient being imaged changes. Moreover, the approach is optionally used for identifying multiple phases accurately across a differing patient population. Alternatively, another specific application is to identify that point in the cardiac cycle when the heart is most stationary. Imaging of the heart at this point minimizes motion artifacts otherwise generated, and, in turn, results in superior visualization of the heart.

Typically, previous developed methods use a fixed absolute delay or alternately a fixed percentage delay from a readily pinpointed time in the cardiac cycle (e.g., the R wave in the electrocardiogram (ECG) waveform) to identify or determine when the heart is at a given phase in the cardiac cycle. However, when these approaches are extended to generating images of multiple phases, it leads to dividing the cardiac cycle into equal parts. Because of the complex motion of the heart different parts of the heart cycle are affected differently with variations in the heart rate. That is to say, e.g., at progressively faster heart rates the diastole portion of the heart cycle becomes progressively shorter in length while the systole portion remains largely unchanged. Consequently, using a fixed delay (either an absolute delay or a percentage of the cardiac cycle) is not sufficiently adapted to locating the same desired phase from cycle to cycle when a patient has a dynamically changing heart rate during the scan. This approach becomes even more difficult when used across populations of patients having differing physiological characteristics. Further difficulties are encountered when fixed delay cardiac imaging is undertaken using an imaging apparatus having longer acquisition times and more stringent temporal demands (e.g., conventional CT scanners).

Accordingly, the present invention contemplates a new and improved technique for cardiac imaging which overcomes the above-referenced problems and others.

SUMMARY OF THE INVENTION

In accordance with one aspect of the present invention, a method of cardiac gating for use in an imaging apparatus is provided. The method includes monitoring a patient's cardiac cycle, and determining a cardiac cycle time for the patient. A desired cardiac phase of interest is selected, and a delay from a reference point in the cardiac cycle is determined. The delay is a function having a nonlinear relationship with respect to at least one of the selected cardiac phase and the cardiac cycle time. Finally, the selected cardiac phase is located in the cardiac cycle using the delay.

In accordance with another aspect of the present invention, a medical diagnostic imager includes an imaging apparatus which scans a patient to acquire image data from the patient. An image processor receives the image data from the imaging apparatus and reconstructs therefrom an image representation of the patient. Also included is a rendering engine which provides the image representation in a human-viewable format. Cardiac gating means control at least one of the imaging apparatus and the image processor such that the image representation obtained coincides with a desired cardiac phase of the patient. The cardiac gating means compensates for nonuniform changes in the patient's cardiac cycle corresponding to a nonuniform distribution of cardiac phases in the patient's cardiac cycle.

One advantage of the present invention is accurate positioning of an acquisition window to image one or more desired phases of the heart.

Another advantage of the present invention is compensation for motion artifacts in cardiac images.

Yet another advantage of the present invention consistent identification and imaging of the same desired heart phase from cycle to cycle in a patient having a dynamically changing heart rate during the imaging scan.

Another advantage of the present invention is its generality for use with multiple image modalities, and its adaptability for use with patients having differing physiologies.

Another advantage of the present invention is that accuracy and repeatability is achieved when more than one phase of the heart is being imaged.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
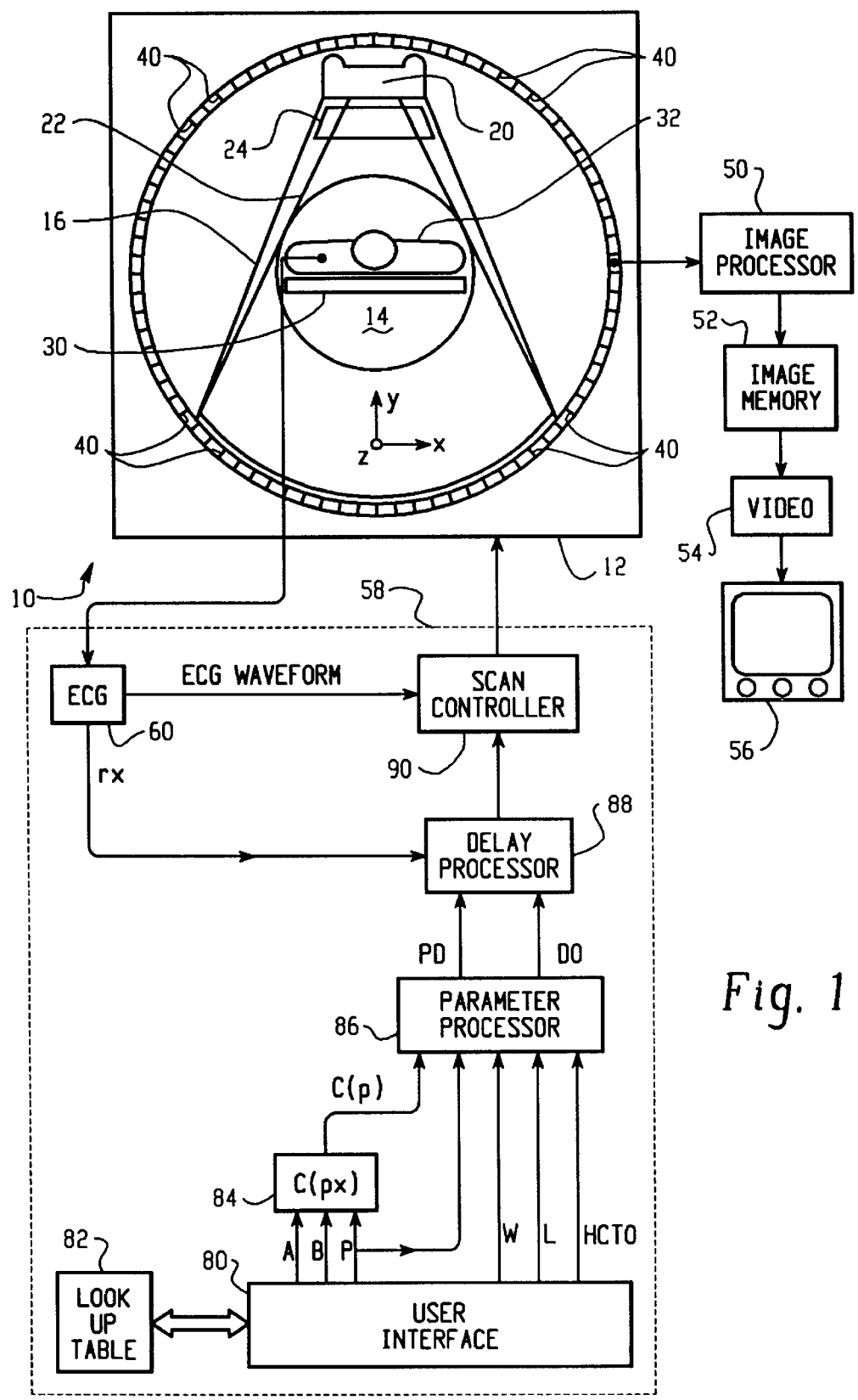
FIG. 1 is a diagrammatic illustration showing a CT scanner with dynamic cardiac gating in accordance with aspects of the present invention.

With reference to FIG. 1, a CT scanner 10 includes a first gantry portion 12 which defines an examination region 14 having a central axis extending in the z direction. A rotating gantry portion 16 is mounted on the first gantry portion 12 for rotation about the examination region 14. A penetrating radiation source 20, such as an x-ray tube, is arranged on the rotating gantry portion 16 such that a beam of radiation 22 passes through the examination region 14 as the rotating gantry portion 16 rotates. A collimator and shutter assembly 24 forms the beam of radiation 22 into a thin fan-shaped beam and selectively gates the beam 22 on and off. Alternately, the fan-shaped radiation beam 22 may also be gated on and off electronically at the source 20.

A patient support 30, such as a couch or the like, suspends or otherwise holds a patient 32 being examined or imaged at least partially within the examination region 14. Optionally, in a spiral scanner or spiral mode, as the rotating gantry portion 16 rotates, the support 30 and/or the first gantry portion 12 are translated in the z direction relative to one another such that the patient 32 on the support 30 is translated along the z direction relative to the source 20. In this manner, the source 20 follows a helical path relative to the patient 32.

In the illustrated fourth generation scanner, a ring of radiation detectors 40 are mounted peripherally around the examination region 14 on the first gantry portion 12. Alternately, a third generation scanner is employed with the radiation detectors 40 mounted on the rotating gantry porion 16 on a side of the examination region 14 opposite the source 20 such that they span the arc defined by the fan-shaped beam 22. Regardless of the configuration, the radiation detectors 40 are arranged to receive the radiation emitted from the source 20 after it has traversed the examination region 14.

In an alternate embodiment, there are multiple sets of radiation detectors 40 residing in separate corresponding parallel planes. The planes are displaced from one another in the z direction. In a fourth generation scanner, this configuration is achieved by having multiple rings (each ring displaced from one another in the z direction) of radiation detectors 40 mounted peripherally around the examination region 14 on the first gantry portion 12. In a third generation scanner, similarly, multiple arcs of radiation detectors 40 are employed. When multi-ring or multi-arc configurations are employed, the beam 22 employed is, e.g., a cone beam arranged to diverge in two dimensions.

In a source fan geometry, an arc of detectors which span the radiation emanating from the source 20 are sampled concurrently at short time intervals as the source 20 rotates behind the examination region 14 to generate a source fan view. In a detector fan geometry, the detectors are sampled a multiplicity of times as the source 20 rotates behind the examination region 14 to generate a detector fan view. The path between the source 20 and each of the radiation detectors 40 is denoted as a ray.

The radiation detectors 40 convert the detected radiation into electronic data. That is to say, each of the radiation detectors produces an output signal which is proportional to an intensity of received radiation. Optionally, a reference detector may detect radiation which has not traversed the examination region 14. A difference between the magnitude of radiation received by the reference detector and each radiation detector 40 provides an indication of the amount of radiation attenuation along a corresponding ray of a sampled fan of radiation.

In detector fan geometry, each view or data line represents a fan of rays having its apex at one of the radiation detectors 40 collected over a short period of time as the source 20 rotates behind the examination region 14 from the detector. In source fan geometry, each view or data line represents a fan of rays having an apex at the source 20 collected by concurrent sampling of all detectors.

In the usual manner, the generated views or data lines from the radiation detectors 40 are acquired from the CT scanner 10, and processed by an image processor 50. The image processor 50 receives sampled data, and optionally shuffles the data to transform it from a detector fan geometry to a source fan geometry or vice versa. An optional ripple filtering operation is also performed. In any event, as is known in the art, the image processor generates images (preferably, of the patient's heart and/or surrounding anatomy) from the acquired views or data lines using known image reconstruction and backprojection techniques. More specifically, the image reconstruction involves mathematical manipulations which convolve each data set with an appropriate filter or convolution function for the view format. The convolved data sets are preferably backprojected into an image memory 52. Ultimately, a video processor 54 selectively retrieves slices, projections, three-dimensional (3D) renderings, and other image information from the image memory 52 and appropriately formats an image representation for display in a human-viewable format on a video monitor 56 or other rendering engine.

Via leads attached to the patient 32, an ECG monitor 60 (preferably digital) acquires ECG data from the patient 32. Alternately, the heart may be monitored via another device such as, e.g., an echo heart monitor, an ultra-sound heart monitor, a heart sound monitor, a pulse oximeter, etc.

Figure 2:
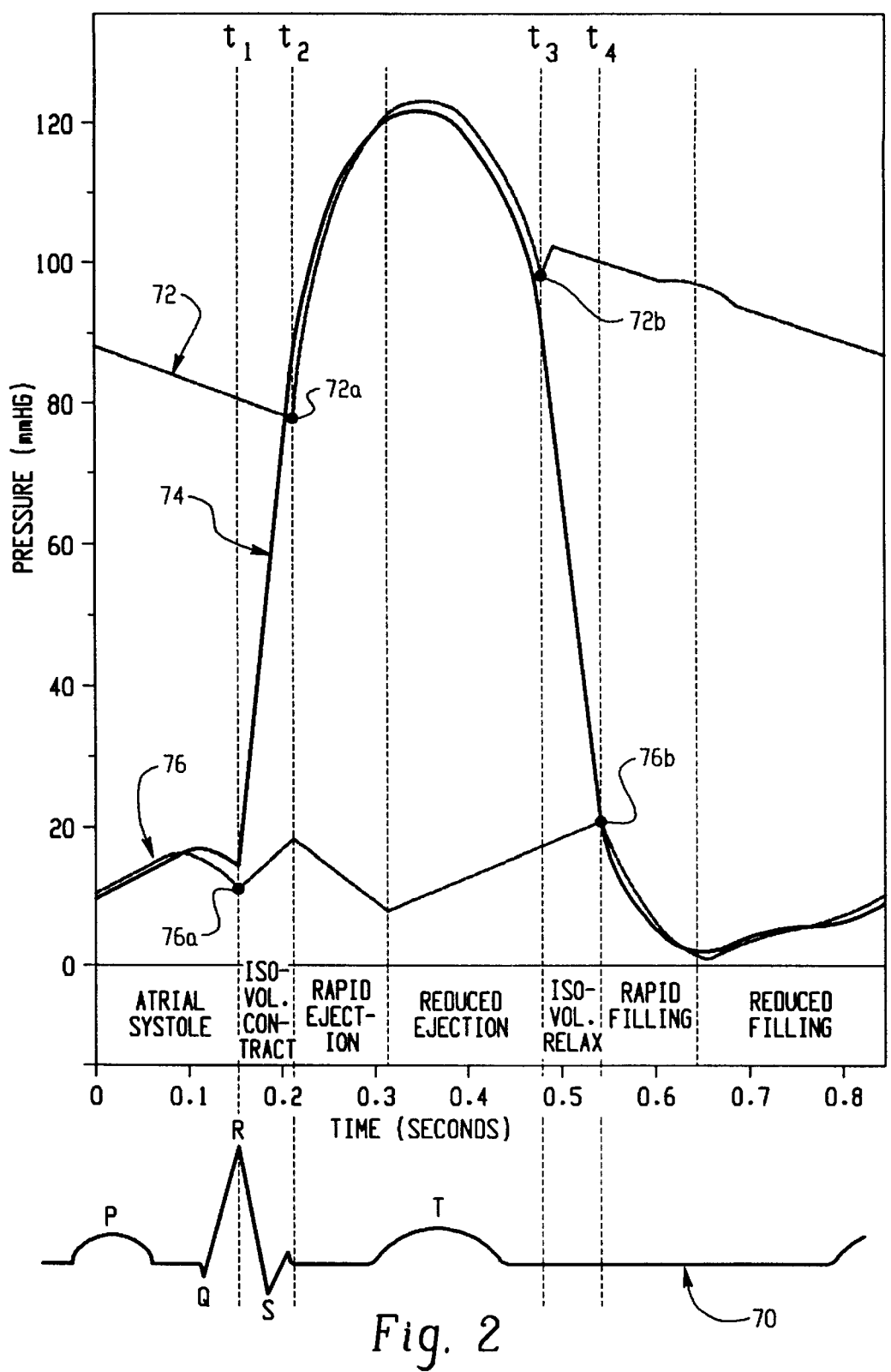
FIG. 2 is a graph of pressure verse time for cardiac anatomy showing in conjunction therewith a corresponding ECG waveform.

With further reference to FIG. 2, a graph of pressure versus time for cardiac anatomy is shown in conjunction with a corresponding ECG waveform 70. Curve 72 represents aortic pressure with respect to time, curve 74 represents left ventricular pressure with respect to time, and curve 76 represents left atrial pressure with respect to time. The starting and end points for both the systole and diastole phases of the cardiac cycle are marked on the waveform. As shown in FIG. 2, times t1 through t4 correspond to the following:

time t1 marks the end of the diastole phase of the cardiac cycle and the start of isovolumic contraction, t1 also coincides with the closing of the AV valves, which event is shown at point 76a on curve 76;

time t2 marks the start of the systole phase of the cardiac cycle, t2 also coincides with the opening of the aortic valve, which event is shown at point 72a on curve 72;

time t3 marks the end of the systole phase of the cardiac cycle and the start of isovolumic relaxation, t3 also coincides with the closing of the aortic valve, which event is shown at point 72b on curve 72; and, time t4 marks the start of the diastole phase of the cardiac cycle, t4 also coincides with the opening of the AV valves, which event is shown at point 76b on curve 76. Various parts of the waveform 70, including the P, Q, R, S, and T waves, are also labeled. The R wave signifies the start of the isovolumic contraction phase or period. For purposes herein, the cardiac cycle will be referred to as beginning at an R wave, and ending at the next following R wave. That is, each cardiac cycle starts at an R wave peak and ends at the next following R wave peak. However, an alternate reference point in the cardiac cycle may be chosen with the cardiac cycle time being the time between adjacent reference points. The timing of each event shown in FIG. 2 is for a healthy heart beating at approximately 75 beats per minute (bpm). FIG. 2 shows a complete cardiac cycle.

From historical data and other sources, some basic characteristics or patterns have been observed regarding the manner in which ECG signals correspond to the motion of the heart, and the manner in which various cardiac phases are affected by variations in heart rate and variations across patient populations. For example, it has been observed that roughly the first third of the cardiac cycle is the systolic phase, where the heart contracts actively to pump the blood out into the aorta (e.g., in an individual having a heart rate of 60 bpm, the first 300–400 milliseconds (msec) of the heart cycle corresponds to the systolic phase). Additionally, for a given patient, as the heart rate changes, the diastolic phase of the heart is affected more (i.e., has greater variation in its duration) than the systolic phase of the heart. That is, an increase or decrease in heart rate does not necessarily result a linear compression or expansion of the ECG waveform 70. Also, there are two sub-phases during the diastolic phase of the cardiac cycle know as the rapid filling (RF) phase and the atrial systole (AS) phase. It has been observed that for normal, younger patients the RF phase is dominant, and conversely, for older patients or patients with certain types of cardiac disease, the AS phase dominates. It is also preferred, that each phase imaged in a cardiac cycle should lie entirely within one R wave interval, i.e., the last phase imaged should not cross or overlap into the next R wave interval.

In one preferred embodiment of the present invention, a dynamic algorithm or model has been developed, optionally based in part on the observed characteristics or patterns set forth above. The dynamic algorithm or model is used to accurately and consistently identify one or more desired phases of the heart as the heart rate varies. Moreover, the model is readily adapted for different patient populations. Preferably, the model is implemented via a software configuration, a hardware configuration, or a combination of both.

In a preferred embodiment, the goal is to identify for imaging one or more desired cardiac phases, for example, so called anchor phases such as the mid-systolic phase and mid-diastolic phase, or optionally a plurality of phases in-between. Because of the lack of a unique signature in the ECG signal at these locations, with prior developed techniques, it is difficult to locate these phases consistently from cycle to cycle as the heart rate is changing dynamically over time. Further difficulty is encountered when trying to locate these cardiac phases across different patient population. For example, the start of the diastole phase is marked as sometime after the T wave, but there is no unique signature in the ECG waveform to identify that phase. Even if the various phases of the heart rate are identified for a given heart rate and for a given patient population, this changes with changes in heart rate and/or changes in the patient population.

Figure 3:
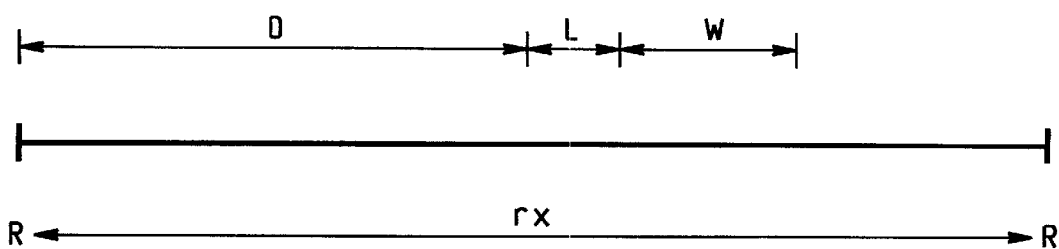
FIG. 3 is a time line showing dynamic algorithm or model parameters employed in accordance with aspects of the present invention.

Accordingly, the dynamic algorithm or model in accordance with aspects of the present invention that accurately and consistently identifies the desired phase or phases of the heart can be understood in terms of the exemplary time line shown in FIG. 3. The time line of FIG. 3 shows one complete cardiac cycle from R wave peak to R wave peak, where "R" represents each R wave peak. The parameter "rx" represents the instantaneous cardiac cycle time or the cardiac cycle period, preferably in milliseconds. That is, rx is the inverse of the heart rate or heart beat frequency. Accordingly, rx varies as the heart rate changes over time. In a preferred embodiment, rx is calculated, determined or otherwise obtained from the ECG monitor 60.

The parameters "L" and "W" represent the latency and acquisition window, respectively, both preferably in milliseconds. Latency is the time which elapses between a request to initiate imaging, and the actual onset of the acquisition of image data from the CT scanner 10 or other imaging apparatus being employed. The acquisition window is the amount of time it takes for enough data to be acquired from the CT scanner 10 or other imaging apparatus being employed such that the desired image can be reconstructed. In a spiral or retrospective application, the window defines that portion of the acquired image data which corresponds to the desired phase.

The values of the parameters L and W are preferably predetermined or otherwise selected depending on the imaging apparatus and image modality being employed. For example, in the case of real-time zero latency acquisition, L and W are both zero. In any event, by adjusting the values of the L and W parameters appropriately, the dynamic algorithm or model can be tuned to the particular imaging apparatus and/or modality of choice.

The parameter "D" is the calculated or otherwise determined delay that identifies, or results in the imaging of, a desired cardiac phase. Mathematically, the delay D is preferably given by the following equation:

$$D(rx,\ px) = px^*[HCT0 + C(px)^*(rx - HCT0)] - W/2 - L \qquad (1);$$

wherein "HCT0" represents a reference heart rate, preferably, an expected average or mean heart rate. Optionally, HCT0 is an adjustable parameter which is set or selected based the particular application and/or circumstances.

In accordance with equation (1), D is a function of rx and "px" where px is a variable representing the desired phase of the heart to be located and/or imaged. Preferably, px is a variable having a value ranging from 0 to 1, wherein, 0 represents the heart's phase at the very beginning of the cardiac cycle, and 1 represents the heart's phase at the very end of the cardiac cycle. Accordingly, as px is varied or selected to locate and/or image desired phases of the cardiac cycle, a delay D is calculated for the corresponding cardiac phase based on the instantaneous heart cycle time and the compliance (described below) for the selected px. From cycle to cycle, each calculated D can then be used to accurately and consistently identify, locate and/or image the cardiac phase to which it corresponds.

Figure 4A:
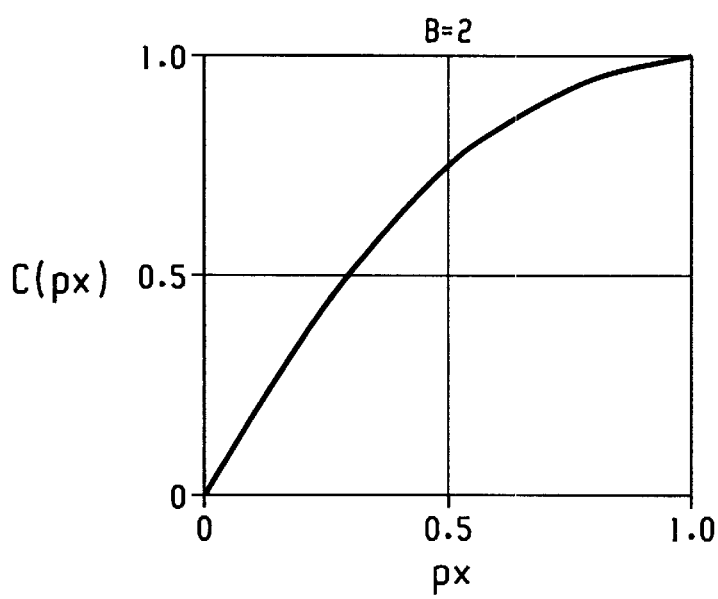
FIG. 4A is a graph of a compliance curve employed in accordance with aspects of the present invention, shown with parameter B=2.0; and, FIG. 4B is a graph of a compliance curve employed in accordance with aspects of the present invention, shown with parameter B=1.0.
Figure 4B:
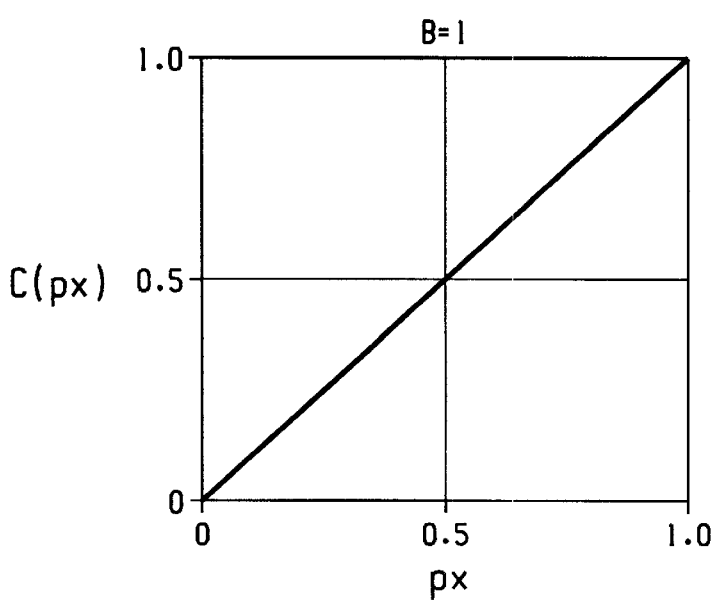

One of the components of equation (1) is the compliance term, C(px). FIGS. 4A and 4B are plots of exemplary compliance curves with respect to px. Preferably, the compliance curve is mathematically given by the following equation:

$$C(px) = [1 - A(1-px)^B] \qquad (2);$$

wherein "A" and "B" are preferably adjustable compliance tuning factors or parameters. For example, the compliance curve as defined by equation (2), with A=1.0 and B=2.0, shows that for px close to zero, the value of compliance is very small, and, hence, an absolute fixed delay model is achieved (see FIG. 4A). This is consistent with the previously noted characteristic that as the heart rate changes the systolic phase does not change much, at least in comparison to the diastolic phase. On the other hand, as the px value increases, and one gets into the diastolic phase, the curve more closely emulates actual physiologic conditions in that region insomuch as the diastolic phase gets affected more as the heart rate changes. The parameters A and B in the compliance equation above determine the shape of the compliance curve, C(px).

In the above example, A=1.0, and B=2.0. With reference to FIG. 4B, another exemplary compliance curve is shown with A=1.0, and B=1.0. Accordingly, from equation (2) above it is clear that by changing the parameters A and B the dynamic algorithm or model can be used to fit different physiologic characteristics, and different imaging modalities. That is to say, changing the parameters A and B, for example, makes the dynamic algorithm or model adapt to different physiologic cases. As described above, cardiac phases may vary based on the patient population. The two physiological cases described above shows a difference based on age or specific cardiac conditions. In the two different populations, the diastolic phases of importance are different, i.e., one of the two anchoring phases is at a different location. For younger patients, it is towards the end of the diastole period, while for the older patients, it more towards the middle of the diastole period. This model adapts easily to these changes. For example, the model works well for the normal, young patient wherein "rapid filling" dominates the diastolic phase by setting the parameter B equal to, e.g., 2.0, while for the older patients, changing the parameter B to, e.g., 1.0 generally fits their physiologic condition better.

In a preferred embodiment, the dynamic algorithm or model is implemented in a device. In doing so, the above model is optionally restated as to a two-parameter model for a given phase of the heart cycle. In this manner then, the above equation (1) is preferably rewritten as:

$$D(rx)=rx(PD/100)+DO \quad (3);$$

where, $$PD=\text{round}(100P*C(P)) \quad (4);$$

and $$DO=\text{round}[HCT0*P*(1-C(P))-(W/2)-L] \quad (5);$$

where "P" is the selected or otherwise chosen value of px representing the desired or chosen cardiac phase, and the "round" function is a function which rounds off the argument or value on which it operates to a determined place. The final delay D calculated or otherwise determined for a particular desired phase, based on equation (3) above, is now a linear combination two parameters "PD" and "DO" which represent, respectively, a percentage delay out of 100% and a delay offset (preferably in millisecond). With this implementation of the model, it is readily incorporated into a device (e.g., an ECG machine) where the parameters PD and DO change based on what cardiac phase one is interested in.

In any event, there are numerous cardiac imaging applications that benefit from the dynamic algorithm or model described above. Without loss of generality, some conventional CT based applications are now described.

CT scanner are typically used in two modes to image the heart, one approach employs Axial Prospective Gated Scans (APGS), and another employs Spiral Retrospective Gated Scans (SRGS). In APGS, the images are acquired in the so called axial scanning mode, and the images are gated to the specific phase of interest. Often, the aim is to identify the phase of the heart that has the least motion. This allows for superior imaging of the heart with minimized motion artifacts. It is used for reliable calcification scoring. The challenge is that during the scan time the heart rate of the patient 32 varies, and it is difficult to image the heart at the same phase in successive cycles. Using the approach of the present invention this problem is considerably diminished. For example, if the aim is to acquire images during the end-diastolic phase, the PD and DO parameters can be calculated and used as input to then generate a trigger at the appropriate time based on the current heart rate.

In SRGS, the images are acquired in the so called spiral mode. The scan data is tagged with the ECG signal. The aim here is to identify the appropriate multiple phases of the heart automatically. As discussed above the anchoring phases could be, for example, the mid-systolic phase and the mid-diastolic phase. The model proposed above can be used to identify these locations. Once identified the heart can be reconstructed at multiple phases of the cardiac cycle. One of the phases, for example, the mid-diastolic phase is then used to analyze the coronary arteries directly to evaluate stenosis. On the other hand, multiple phases of the heart could be used to study wall motion abnormalities, valve motion abnormalities, ejection fraction, and other critical cardiac parameters.

Being able to identify a cardiac phase for a patient more accurately and reliably also allows for functional imaging where a particular phase of the heart might be studied more closely for a certain abnormality. This phase of the heart can be identified for the patient over a period of time during follow up visits to the cardiologist.

In alternate embodiments of invention, different parameters are used to define different compliance curves which simulate different variations in patients based on age, cardiac disease, gender, etc. The compliance curve is also adjusted to take into consideration variations for imaging directed to different parts of the heart which move differently. The delays calculated for imaging the most stationary phase of the heart is a special case of the above generalized model.

Returning attention to FIG. 1, a preferred embodiment of the present invention for prospective cardiac gating is shown. A user interface 80 is employed to permit selection of the model parameter W, L, HCT0, P, A, and B. The parameters are optionally set manually by the operator via the interface 80. Alternately, the operator inputs factors consistent with the application (e.g., patient information, imaging apparatus, image modality, and the cardiac phase of interest) and the model parameters are automatically selected, e.g., from a look up table 82.

The model parameters are then passed forward. P, A and B are input into a compliance processor 84 which calculates or otherwise determines C(P) in accordance with equation (2). W, L, HCT0, P and C(P) are then input into a parameter processor 86 which calculates or otherwise determines PD and Do in accordance with equations (5) and (6). The parameters PD and DO are then input into a delay processor 88 along with the instantaneous cardiac cycle time or period, rx, obtained from the ECG monitor 60. Based on the input thereto, the delay processor 88 calculates or otherwise determines, in accordance with equation (3), the delay D for the cardiac phase of interest.

A scan controller 90 is provided with the delay D form the delay processor 88 and the ECG waveform 70 from the ECG monitor 60. The scan controller 90 controls operation of the CT scanner 10 in response to the ECG waveform 70 and the delay D. More specifically, the scan controller 90 triggers operation the scanner 10 after a delay period D following each R wave peak such that image data corresponding to the cardiac cycle of interest is generate by the CT scanner 10 and acquired from the detectors 40. That is, the scanner 10 is caused to operate or generate data when the heart is in the desire phase. In this manner, the imaging apparatus is gated so that the captured image corresponds to the time when the heart is in the desire phase of interest.

In an alternate preferred embodiment, the dynamic algorithm or model in accordance with the present invention is employed retrospectively. That is to say, the image data is acquired continuously throughout the cardiac cycle and saved. As the data is acquired it is correlated and tagged with the ECG waveform 70 from the monitor 60. The model is then employed to locate and/or identify the different phases of the heart corresponding to the tagged data. In this manner, the desire cardiac phase or phases of interest can be selectively reconstructed into a human-viewable images using the data identified or located by the model.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of cardiac gating for use in an imaging apparatus, said method comprising:
    (a) monitoring a patient's cardiac cycle;
    (b) determining a cardiac cycle time for the patient;
    (c) selecting a desired cardiac phase of interest;
    (d) determining a delay from a reference point in the cardiac cycle, wherein the delay is a function having a nonlinear relationship with respect to at least one of the selected cardiac phase and the cardiac cycle time; and,
    (e) locating the selected cardiac phase in the cardiac cycle using the delay.

2. A method of cardiac gating for use in an imaging apparatus, said method comprising:
    (a) monitoring a patient's cardiac cycle;
    (b) determining a cardiac cycle time for the patient;
    (c) selecting a desired cardiac phase of interest;
    (d) determining a delay from a reference point in the cardiac cycle, wherein the delay is a function having a nonlinear relationship with respect to at least one of the selected cardiac phase and the cardiac cycle time, the function being mathematically expressed as:

$$D(rx, px) = px*[HCT0+C(px)*(rx-HCT0)]-W/2-L$$

where D represents the determined delay, rx is a variable representing the cardiac cycle time, px is a variable representing the selected cardiac phase, HCT0 is a parameter representing a reference heart rate, C(px) is an adjustable compliance function, W is an acquisition window duration, and L is a latency duration; and,
    (e) locating the selected cardiac phase in the cardiac cycle using the delay.

3. The method according to claim 2, wherein the adjustable compliance function is mathematically expressed as:

$$C(px)=[1-A(1-px)^B]$$

where A and B are adjustable parameters which control a shape of the compliance function to fit particular applications.

4. The method according to claim 2, wherein the adjustable compliance function is adjusted to model the patient's particular physiology.

5. The method according to claim 1, further comprising:
    (f) identifying collected image data corresponding to the desired phase of interest.

6. The method according to claim 1, further comprising:
    (f) triggering the imaging apparatus to collect image data following the delay.

7. The method according to claim 1, wherein the determined delay compensates for nonuniform changes in the cardiac cycle resulting from changes in the patient's heart rate.

8. A medical diagnostic imager comprising:
    an imaging apparatus which scans a patient to acquire image data from the patient;
    an image processor which receives the image data from the imaging apparatus and reconstructs therefrom an image representation of the patient;
    a rendering engine which provides the image representation in a human-viewable format; and,
    cardiac gating means for controlling at least one of the imaging apparatus and the image processor such that the image representation obtained coincides with a desired cardiac phase of the patient, wherein said cardiac gating means dynamically adjusts a delay to compensate for nonuniform changes in a distribution of cardiac phases within the patient's cardiac cycle resulting from changes in the patient's heart rate.

9. The medical diagnostic imager according to claim 8, wherein the imaging apparatus is a CT scanner.

10. The medical diagnostic imager according to claim 8, wherein the cardiac gating means includes:
    a monitoring device which monitor's the patient's cardiac cycle, said monitoring device being selected from the group consisting of an ECG monitor, an echo heart monitor, an ultra-sound monitor, a heart sound monitor, and a pulse oximeter.

11. The medical diagnostic imager according to claim 10, wherein the cardiac gating means further includes:
    delay determining means which determine the delay from a reference point in the cardiac cycle, said delay being used to locate the desired cardiac phase in the cardiac cycle, wherein the delay is a function of the desired cardiac phase and a cardiac cycle time obtained from the monitoring device.

12. The medical diagnostic imager according to claim 11, wherein the function is mathematically expressed as:

$$D(rx, px) = px*[HCT0+C(px)*(rx-HCT0)]-W/2-L$$

where D represents the determined delay, rx is a variable representing the cardiac cycle time, px is a variable representing the selected cardiac phase, HCT0 is a parameter representing a reference heart rate, C(px) is an adjustable compliance function, W is an acquisition window duration, and L is a latency duration.

13. The medical diagnostic imager according to claim 12, wherein the adjustable compliance function is mathematically expressed as:

$$C(px)=[1-A(1px)^B]$$

where A and B are adjustable parameters which control a shape of the compliance function to fit particular applications.

14. The medical diagnostic imager according to claim 12, wherein the delay determining means includes:
a two-parameter delay processor which determines the delay in accordance with the following equation:

$$D(rx)=rx(PD/100)+DO$$

where, parameter PD=round(100P*C(P)) and parameter DO=round[HCT0*P*(1−C(P))−(W/2)−L]; and, where P represents a value for px corresponding to the desired cardiac phase, and round is a function which rounds off its argument to a given place.

15. The medical diagnostic imager according to claim 11, wherein the delay has a nonlinear relationship with respect to at least one of the desired cardiac phase and the cardiac cycle time.

16. The medical diagnostic imager according to claim 12, wherein the adjustable compliance function is adjusted to model the patient's particular physiology.

17. The medical diagnostic imager according to claim 8, wherein the cardiac gating means includes:

a scan controller which triggers operation of the imaging apparatus such that the image data is acquired from the patient at a time that coincides with the desired cardiac phase.

18. A cardiac monitoring device comprising:

a delay processor which computes a duration from a reference point in a cardiac cycle to a desired point in the cardiac cycle, said delay processor computing the duration such that nonuniform shifting of phases in the cardiac cycle's phase distribution resulting from changes in heart rate are accounted for.

19. The cardiac monitoring device of claim 18, wherein the delay processor computes the duration based upon two variable parameters input into the delay processor.

* * * * *